United States Patent
Takeuchi et al.

(10) Patent No.: US 7,592,465 B2
(45) Date of Patent: Sep. 22, 2009

(54) FERTILIZER/PLANT VITALIZER

(75) Inventors: Makoto Takeuchi, Kawasaki (JP); Yuki Miyazawa, Kawasaki (JP); Hiroyuki Sato, Kawasaki (JP); Masazumi Date, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 29 days.

(21) Appl. No.: 11/466,789

(22) Filed: Aug. 24, 2006

(65) Prior Publication Data

US 2007/0197392 A1 Aug. 23, 2007

(51) Int. Cl.
*C07D 207/28* (2006.01)
(52) U.S. Cl. .................................. 548/535; 435/420
(58) Field of Classification Search ................ 504/283; 548/535; 435/420
See application file for complete search history.

(56) References Cited

U.S. PATENT DOCUMENTS

| 5,120,652 | A | * | 6/1992 | Groeger et al. ............. 435/228 |
| 5,219,741 | A | * | 6/1993 | Groeger et al. ............. 435/107 |
| 6,171,869 | B1 | * | 1/2001 | Safarian et al. ............. 436/178 |
| 2004/0192553 | A1 | | 9/2004 | Kurauchi et al. |
| 2006/0228396 | A1 | * | 10/2006 | Ohta et al. .................. 424/439 |

FOREIGN PATENT DOCUMENTS

| JP | 46-42566 | 12/1971 |
| JP | 56-32951 | 7/1981 |
| JP | 57-002691 | 1/1982 |
| JP | 59-066893 | 4/1984 |
| JP | 03-201914 | 9/1991 |
| JP | 04-058825 | 2/1992 |
| JP | 04-058833 | 2/1992 |
| JP | 06-080530 | 3/1994 |
| JP | 08-157317 | 6/1996 |
| JP | 2001-131009 | 5/2001 |
| JP | 2001-192310 | 7/2001 |
| JP | 2002-199812 | 7/2002 |
| JP | 2003-048803 | 2/2003 |
| WO | WO03/013240 | 2/2003 |

OTHER PUBLICATIONS

Pyo, S., Expression and Purification of a Rcombinant Bforin Drivative from *Escherichia coli*, Process Biochemistry 39 (2004), Elsevier, pp. 1731-1736.*
Srivastava, S., Understanding Bacteria, Springer, 2003, pp. 116-117, ISBN 1402016336.*
International Preliminary Report on Patentability for PCT Patent App. No. PCT/JP2005/003015 (Sep. 28, 2006).
International Search Report for PCT App. No. PCT/JP2005/003015 (May 17, 2005).

* cited by examiner

*Primary Examiner*—Johann R Richter
*Assistant Examiner*—Danielle Sullivan
(74) *Attorney, Agent, or Firm*—Shelly Guest Cermak; Cermak Kenealy Vaidya & Nakajima LLP

(57) ABSTRACT

Contamination by microorganism of an aqueous proline solution is prevented by adjusting a proline concentration of the solution to 20% (W/W/) or more. Such solutions are useful as fertilizers and/or plan vitalizers. Preservation of the novel solutions are possible over a significant period of time, allowing for more flexibility in the distribution and application of commercial products made from the solutions.

8 Claims, No Drawings

FERTILIZER/PLANT VITALIZER

This application claims priority under 35 U.S.C. §119(a) to JP2004-050810, filed Feb. 26, 2004, and under 35 U.S.C. §120 to PCT/JP2005/03015, filed Feb. 24, 2005, the entireties of which are incorporated by reference.

BACKGROUND OF THE INVENTION

1. Field of the Invention

The present invention relates to a composition composed of an aqueous solution of L-proline (hereinafter, sometimes simply referred to as "proline"), which is useful as a fertilizer and/or plant vitalizer. In addition, the present invention relates to a method for preserving the aqueous proline solution while avoiding contamination by microorganims. Furthermore, the present invention allows for superior distribution to plants and soil of the novel compositions formulated as commercial products due to their superior preservation.

2. Brief Description of the Related Art

Proline is an amino acid which is known to be effective as a fertilizer or a plant vitalizer (see Japanese Publication No. JP-A 2001-131009). Products containing proline advertising these effects are currently being sold.

To date, proline has been used as a raw material in pharmaceuticals and foods, and therefore is present in a large number of products. However, proline is typically in a crystalline or a powdery state, so it is preserved, distributed, and sold in products as a solid, with almost no moisture content. Among these products, Hanakagami (trade name) (Shoko Co., Ltd.) is a product which contains a high percentage of proline, and which is currently sold in Japan as a fertilizer or a plant vitalizer. Similarly, Hanakagami is preserved, distributed, and sold in a solid powdery state.

Proline products which are preserved, distributed, and sold as solids suffer from caking and deliquescence, due to the high hygroscopic property of proline, which greatly deteriorates the quality of the products. In order to avoid these problems, and to prevent moisture absorption by the proline, conventional solid commercial products are required to include a silica gel having a hygroscopic property stronger than that of the proline, or be packed in a packaging material such as an expensive aluminized film which has almost no moisture permeability.

The main reason proline is distributed as a solid despite the cumbersome burden and cost as described above is that liquid proline solutions easily decomposes and rots from exposure to microorganisms. In other words, many amino acids, including proline, when in aqueous solution without an additive which prevents microbial contamination, such as a preservative or a microbicide, start to gradually decompose due to microbial contamination within several days because of their high nutritive value. This effect is even seen when proline is in a normal preservation environment, but not an aseptic environment. If these problems did not exist, liquid proline is preferable when used in fertilizer or plant vitalizer formulations, because it is excellent in operability and ease of distribution.

Accordingly, there are only a few known methods for preservation and/or distribution, or a proline product useful as a fertilizer or a plant vitalizer, particularly a proline product in a liquid state. Typically, an additive, such as a preservative or a microbicide, is always added to the liquid containing proline in order to prevent microbial contamination.

For instance, Japanese Publication No. JP-B 46-42566 describes that a hydrolysate of proline or of a protein containing proline, an amino acid mixture, or the like is used as the source of proline for a flower-bud formation accelerator which contains a combination of proline and uracil. However, it appears that liquid proline was not used as the raw material in preparation of the flower-bud formation accelerator.

Meanwhile, Japanese Publication No. JP-B 56-32861 describes a solution obtained by decomposing proteins of soybean, a cereal grain, a microbial cell body, or the like by various methods, fermentation solutions of various amino acids, and the like, all of which include proline. However, there is no description about how the proline-containing solutions are preserved and/or distributed.

In addition, Japanese Patent No. 2852677, Japanese Patent No. 2874788, and Japanese Patent No. 2874789 describe an amino acid fermentation solution containing proline, alanine, valine, glutamic acid, and the like, which has been subjected to the removal of cell bodies or sterilization. This solution is intended to apply to plants. However, there is no specific description about how the amino acid-containing solution is preserved and/or distributed.

Japanese Publication No. JP-A 06-80530 describes that an amino acid fermentation solution to be applied to a plant may include an organic or inorganic material in order to facilitate the storage, transport, or handling of the amino acid fermentation solution. That is, it is described that, in order to cover the shortcomings of the amino acid fermentation solution, an organic material or inorganic material of any appropriate kind for improving the preservability or the ability to be distributed is preferably added. Specific examples of the organic or inorganic material include, when it is a liquid, various alcohols, ethers, ketones, aromatic hydrocarbons, paraffinic hydrocarbons, and aldehydes.

Japanese Patent No. 3377873 describes that a solution which is obtained by removing cell bodies from an amino acid fermentation solution containing various amino acids. This solution undergoes a change in the components due to the proliferation of microorganisms if nothing is added to the solution, except when the solution is used immediately. Therefore, it is preferable that the solution be preserved after the pH thereof is adjusted to 3 or less to stabilize the quality. In general, a large amount of a strong mineral acid such as hydrochloric acid or sulfuric acid has to be added in order to adjust the pH of the resulting fermentation solution so that it has a pH around neutral to 3 or less.

Japanese Publication No. JP-A 2001-192310 describes that a surfactant, a pH regulator, or a preservative may be added to an amino acid fermentation solution, as required. Japanese Publication No. JP-A 2002-199812 describes a proline-containing product which contains a surfactant when used in a liquid form. Furthermore, Japanese Publication No. JP-A 2003-48803 describes that proline-containing products can be blended with a microbicide, a surfactant, or a preservative so to prevent spoilage by microbes.

SUMMARY OF THE INVENTION

The conventionally known problems associated with proline-containing solutions are caused by the use of various additives for suppressing proliferation of contaminating microorganisms which cause deterioration in preservability of the solution.

In general, fertilizers or a plant vitalizers containing proline are applied by mixing or injecting these compositions into cropland soil on which plants are growing, or dispersing onto the parts of the plants which are above ground. Therefore, when a fertilizer or a plant vitalizer containing proline is applied to a plant, the various additives added to the proline-containing solution are concomitantly applied not only to the plants, but also to the surrounding areas. As a result, for example, when a preservative, a microbicide, or the like is applied to field crops, an adverse effect is seen on the growth of various organisms, including beneficial soil bacteria in the farmland. In recent years, various agricultural chemicals and environmental hormones left in the soil have become problematic, and prevention of environmental pollution which accompanies agricultural production is a great social concern.

Furthermore, also when a preservative or a bacteriocide as described above is applied in a facility such as a greenhouse, the influence on the surrounding environment has certainly become problematic, and the adverse effects on the health of workers has resulted in even more problems.

In addition, adding an acid to the proline-containing solution to lower the pH and thereby suppress the proliferation of microorganisms can also result in surrounding environmental destruction, similar to the problems with the addition of a bacteriocide. This is because the acidic solution is dispersed around the plant when the proline-containing solution is applied to the plant.

Furthermore, use of a proline-containing solution in which the pH thereof is decreased by adding an acid, particularly a mineral acid such as hydrochloric acid or sulfuric acid, causes the accumulation of inorganic ions of hydrochloride, sulfide, and the like, in the soil, leading to soil pollution, which is often called salt accumulation. There is a concern that repeated application of such a proline-containing solution for many years may cause salt damage, resulting in inhibition of the growth of plants due to an increase in the salt concentration of the cropland soil.

Environmental pollution is clearly associated with the repeated application of bacteriocides, preservatives, and acidic solutions, even if the proline-containing solutions containing these additives are diluted with a large amount of water, so the essential problems are not solved.

Thus, an object of the present invention is to provide a proline solution to be used as a fertilizer or a plant vitalizer, which has improved preservability, operability, and distribution without using additives which may cause the environmental pollution as described above.

A proline-containing solution has been found which prevents spoilage due to microbial contamination without impairing the operability of the solution. In this solution, the proline concentration in the solution is adjusted to be within an appropriate range.

That is, the present invention is as described hereinbelow.

It is an object of the present invention to provide an aqueous L-proline composition comprising an L-proline concentration of 20% (w/w) or more.

It is a further object of the present invention to provide the composition as described above, wherein the L-proline concentration is 80% (w/w) or less.

It is a further object of the present invention to provide the composition as described above, wherein the L-proline concentration is 40 to 70% (w/w).

It is a further object of the present invention to provide the composition as described above, which is obtained by culturing a microorganism having L-proline-producing ability in a medium, removing cell bodies from the medium, resulting in a L-proline solution, and concentrating the L-proline in the solution.

It is a further object of the present invention to provide the composition as described above, which is obtained by desalting the L-proline solution after removing the cell bodies and before concentrating the L-proline in the solution.

It is also an object of the present invention to provide a method of preserving an aqueous L-proline solution while avoiding contamination by microorganisms, comprising adjusting the concentration of L-proline in the aqueous L-proline solution to 20% (w/w) or more.

It is a further object of the present invention to provide the method as described above, in which the aqueous L-proline solution is obtained by culturing a microorganism having L-proline-producing ability in a medium, removing cell bodies from the medium resulting in an L-proline solution, and concentrating the L-proline in the solution.

It is a further object of the present invention to provide the method as described above, wherein the aqueous L-proline solution is obtained by desalting the L-proline solution after removing the cell bodies and before concentrating the L-proline in the solution.

It is another object of the present invention to provide a composition selected from the group consisting of a fertilizer and a plant vitalizer comprising the compositions as described above.

It is further object of the present invention to provide an environmentally safe method of distributing a composition as described above to soil comprising mixing said composition into said soil.

It is a further of the present invention to provide an environmentally safe method of distributing a composition as described above to plants comprising spraying said composition onto the plant parts which are above ground.

It is a further object of the present invention to provide a method of preventing salt damage to plants comprising applying the composition as described above to said plants.

DESCRIPTION OF THE PREFERRED EMBODIMENTS

Hereinafter, the present invention will be described in detail. Note that, herein, the term "proline" herein refers to "L-proline".

The compositions to be used as a fertilizer or a plant vitalizer for improving the growth of a plant, and the method of applying the composition to the plant are not particularly limited. Typical examples of the plants of interest include flowers and ornamental plants such as roses and pansies; vegetables such as cucumbers, tomatoes, strawberries, melons, and spinach; fruits such as pears, mandarin oranges, and grapes; and cereal grains such as rice and beans. Meanwhile, examples of the application method include mixing or injecting into the soil where the plants are growing, and dispersion onto the above-ground parts of the plants.

The composition is composed of an aqueous L-proline solution having an L-proline concentration of 20% (w/w) or more. (Hereinafter, the composition of the present invention may also be referred to as a "proline solution of the present invention").

In general, when an aqueous solution of an amino acid is subjected, for example, to vaporization for the purpose of adjusting the amino acid concentration or the moisture content, the moisture content in the aqueous solution decreases while the amino acid concentration increases, resulting in an increase in the osmotic pressure of the aqueous solution. As a consequence, many microorganisms cannot survive such an environment in which the osmotic pressure exceeds a level at which the bacteria can survive in the solution. However, the extent to which the moisture content is decreased and the osmotic pressure is increased in order to suppress the proliferation of the microorganisms, such as saprophytic microorganisms, depends on the kind of solution, the kind of solute, physical conditions such as temperature or pH, and the like, and thus is not constant.

On the other hand, the amino acid concentration in the aqueous solution gradually increases as the moisture evaporates, and the dissolved amino acids become crystals and precipitate when the concentration exceeds saturation of the amino acids with respect to water. The amino acid aqueous solution in which the crystal is precipitated cannot maintain its uniformity because the crystal deposits on a bottom portion, and has an inferior operability because the solid component is mixed therein and thus is not preferable for preservation or for distribution. In addition, if the moisture content is further decreased when the crystal precipitates, the amino acid concentration of the solution does not increase. Therefore, if the osmotic pressure at that time is within a range in which a bacterium can proliferate, preventing spoilage of the solution by microbes by further adjustment of the moisture content will most likely not occur.

Accordingly, to date, the methods for preserving and distributing amino acids by adjusting the moisture content in an amino acid aqueous solution to prevent the decomposition of the amino acids by a bacterium, have hardly been put to practical use. In particular, such distribution of proline have not been previously disclosed.

The relationship between the proline concentration in an aqueous proline solution, the growth of contaminating microorganisms in the solution, and the operability of the solution have been investigated. As a result, it has been determined that the proline concentration of a solution can be adjusted to within a particular range, which makes it possible to prevent the proliferation of contaminating microorganisms without impairing the operability of the solution. In addition, the packaging of such products is made compact by increasing the proline concentration, thereby making it possible to improve the distribution in view of its preservation, transport, and the like.

The proline concentration of the solution is preferably 80% (w/w) or less, more preferably 20 to 70% (w/w), and still more preferably 40 to 70% (w/w). A particularly preferable proline concentration is about 50% (w/w). The proline concentration can be adjusted so to prevent the proliferation of contaminating microorganisms. Meanwhile the precipitation of proline during preservation can be prevented, and the viscosity of the proline solution does not become too high. Therefore, physical properties suitable for distributing the solution using a pump or the like or spraying the solution can be maintained.

The proline solution of the present invention can be produced by, for example, dissolving proline in water such that the proline concentration is within the above-mentioned range. The proline solution may contain components other than proline as long as the effectiveness of the solution is not impaired. Examples of the other components include other fertilizer components, plant vitalizers, plant growth regulators, vitamins, minerals, spreaders, and other generally applied agricultural/horticultural materials. However, when the proline solution of the present invention is used as a fertilizer or a plant vitalizer and dispersed onto cropland, the amount of non-proline components is preferably small so to prevent growth inhibition (e.g., salt damage) of the plants and resulting environmental pollution.

The terms "solution" or "aqueous solution" in the present invention means that a solvent is water or a water-based solution. The water-based solution may contain a water-soluble organic solvent such as an alcohol such as ethanol, and the like. The concentration of the water-soluble organic solvent is not particularly limited as long as a certain solubility of proline can be stably maintained. For instance, when the solvent includes ethanol, the concentration thereof is preferably 20% (w/w) or less, and more preferably 10% (w/w) or less.

A more inexpensive raw material may preferably be used as long as the effectiveness of the proline solution is not impaired. An example of such a raw material includes a proline fermentation solution obtained by using a microorganism having an ability to produce proline.

When a proline fermentation solution is used as the raw material for the proline solution of the present invention, the method of adjusting the proline concentration is not particularly limited. For instance, microbial cell bodies in the proline fermentation solution are removed, and then the proline concentration can be adjusted by using a device for removing a moisture, such as a vacuum evaporator or a reverse osmosis membrane. The proline fermentation solution in which the cell bodies have been removed can be supplemented with solid proline, such as a proline crystal or a liquid containing a high concentration of proline, to increase the proline concentration. This increases the proline concentration in the fermentation solution without the cell bodies. Salts, expect proline, are also preferably removed from this solution. Examples of such salts include inorganic salts which are derived from the medium. Examples of the desalting method include an ion-exchange resin treatment, electroosmosis, and a reverse osmosis membrane treatment. The ratio (i.e., weight ratio) of contaminating salts to proline in the proline solution is preferably 1 or less, more preferably 0.5 or less, or still more preferably 0.3 or less.

The proline fermentation solution can be obtained by culturing a microorganism which has an ability to produce L-proline in a medium so that L-proline is produced and accumulates in the medium. The above-mentioned microorganism is not particularly limited as long as it has the ability to produce proline, and examples thereof include bacteria belonging to the genus *Escherichia*, coryneform bacteria, and bacteria belonging to the genus *Serratia*. Specific examples thereof include the following strains, but the present invention is not limited to these strains.

*Escherichia coli* AJ11543 (FERM P-5483) (JP-A 56-144093)

*Escherichia coli* AJ11544 (FERM P-5484) (JP-A 56-144093)

*Brevibacterium lactofermentum* AJ11225 (FERM P-4370) (JP-A 60-87788)

*Brevibacterium flavum* AJ11512 (FERM P-5332) (JP-B 62-36679)

*Brevibacterium flavum* AJ11513 (FERM P-5333) (JP-B 62-36679)

*Brevibacterium flavum* AJ11514 (FERM P-5334) (JP-B 62-36679)

*Corynebacterium glutamicum* AJ11522 (FERM P-5342) (JP-B 36679)

*Corynebacterium glutamicum* AJ11523 (FERM P-5343) (JP-B 62-36679)

The microorganism which can be used in the proline fermentation may be a wild-type strain, or may be a mutant or a recombinant strain obtained by breeding a microorganism to improve the ability to produce proline.

The medium which can be used in the proline fermentation may be one which is conventially used in proline fermentation, and which contains a carbon source, a nitrogen source, inorganic ions, and as required, organic micronutrients such as amino acids and vitamins.

Examples of the carbon source include saccharides such as glucose, fructose, sucrose, and maltose; saccharified starch containing saccharides; sweet potato molasses, beet sugar molasses, high test molasses, organic acids such as acetic acid, and alcohols such as ethanol and glycerine.

Examples of the nitrogen source include nitrogen-containing raw materials such as ammonia gas, ammonia water, ammonium salts, urea, and nitric acid.

The culture conditions are not particularly different from the conventional method of culturing a proline-producing bacterium.

The proline solution of the present invention can be preserved and distributed without being contaminated by microorganisms, by adjusting the proline concentration within the above-mentioned range. Examples of the contaminating microorganism include microorganisms belonging to the genus *Bacillus*, *Aspergillus*, or *Saccharomyces*.

EXAMPLES

Hereinafter, the present invention will be described in more detail by referring to the following non-limiting examples.

Reference Example 1

Production of the Proline Fermentation Solution (1) Proline Fermentation

A proline fermentation solution can be obtained by a method described in Example 2 in JP-A 05-284985. Specifically, it can be produced in a manner as described below.

A liquid medium having the composition shown in Table 1 was prepared and adjusted to a pH of 7.2. Then, 20 ml of the liquid medium was added to a 500-ml shaking flask and heat-sterilized. One platinum loop of cells of *Corynebacterium glutamicum* AJ11522 which had previously been grown on a natural medium plate was inoculated into the liquid medium, and was cultured with shaking at 30° C. for 72 hours. After completion of the culture, typically, 3.4 g/dl of L-proline is present in the culture solution.

The AJ11522 strain is L-isoleucine auxotrophic, and is an L-proline-producing bacterium which has a high citrate synthetase activity (JP-A 05-284985).

TABLE 1

| Component | Concentration |
|---|---|
| Glucose | 10 g/dl |
| $KH_2PO_4$ | 0.1 g/dl |
| $(NH_4)_2SO_4$ | 6.0 g/dl |
| $MgSO_4 \cdot 7H_2O$ | 0.04 g/dl |
| $FeSO_4 \cdot 7H_2O$ | 1 mg/dl |
| $MnSO_4 \cdot 4H_2O$ | 1 mg/dl |
| Biotin | 250 µg/l |
| Thiamine hydrochloride | 500 µg/l |
| Hydrolysate of soybean protein | 0.3 ml/dl |
| Isoleucine | 15 ml/dl |
| $CaCO_3$ (separately sterilized) | 5 g/dl |

Next, the cell bodies were removed from the culture solution with centrifugation. Then, liquid was evaporated from the solution by heat under vacuum using a rotary evaporator, to thereby obtain 1.2 ml of a concentrated solution. The proline concentration in the concentrated solution was about 50 g/dl.

(2) Production of the Desalted, Concentrated Proline Solution

The method of desalting the proline fermentation solution can be performed according to a conventional method. Hereinafter, a method employing an ion-exchange resin is shown as an example.

The proline fermentation was performed by a method described in the above-mentioned section (1) or any other appropriate method. Sulfuric acid was added to 320 ml of the resulting proline fermentation solution (e.g., a solution containing 20 g of proline) until the pH was around 3. Then, the cell bodies were removed by ultrafiltration. 450 ml of the resulting proline solution was passed through 100 ml of a commercially available cationic ion-exchange resin (H type) having strong acidity, which had been loaded onto a column. Proline in the solution is allowed to adsorb to the resin, thereby separating proline from the contaminating anions present in the fermentation solution. Then, an eluting solution of 200 ml of 1 N NaOH was passed through the column, followed by water (typically, about 600 ml) until the proline, including proline which had adsorbed to the resin, is completely eluted from the column. 700 ml of the eluate obtained by the above described methods contained about 16 g of proline in a concentration of about 2.3 g/dl. Furthermore, the desalted solution can be concentrated by heat under vacuum to remove the moisture, to thereby obtain, for example, 32 ml of a proline solution. The proline concentration of the solution was 50 g/dl.

Example 1

Proline Concentration in an Aqueous Proline Solution and the Proliferation of Microorganisms The proliferation of microorganisms in aqueous proline solutions at various concentrations was investigated according to the method described below.

Proline crystals (manufactured by Ajinomoto Co., Inc.), which are typically used as a raw material for pharmaceutical preparations, were dissolved in tap water to obtain proline solutions at the concentrations shown in Tables 2 and 3, to thereby obtain 50 ml of each solution. Then, 0.5 g of unsterilized soil was added to each proline solution to add microorganisms, and the mixtures were preserved in bottles at 25° C. and 40° C. for 4 weeks. Tables 2 and 3 show the proliferation of microorganisms in each proline solution after this time period at the two temperatures.

TABLE 2

Proliferation of microorganisms in aqueous proline solution (preserved at 25° C. for 4 weeks)

| Proline concen- tration (%) | Number of days | | | | | pH of solution on the 28th day | Osmotic pressure (Osm/kg) | Operability of solution |
|---|---|---|---|---|---|---|---|---|
| | 0 | 3 | 7 | 14 | 28 | | | |
| 0 | − | − | − | − | − | 6.6 | 0 | Good |
| 10 | − | + | + | + | + | 6.4 | 0.9 | Good |
| 20 | − | − | + | + | + | 6.5 | 1.8 | Good |
| 30 | − | − | + | + | + | 6.5 | 2.7 | Good |

TABLE 2-continued

Proliferation of microorganisms in aqueous proline solution (preserved at 25° C. for 4 weeks)

| Proline concentration (%) | Number of days 0 | 3 | 7 | 14 | 28 | pH of solution on the 28th day | Osmotic pressure (Osm/kg) | Operability of solution |
|---|---|---|---|---|---|---|---|---|
| 40 | − | − | − | + | + | 6.6 | 3.6 | Good |
| 50 | − | − | − | − | − | 6.9 | 4.5 | Good |

−: no appearance of fungi
+: Appearance of fungi

TABLE 3

Microorganism proliferation in aqueous proline solution (preserved at 40° C. for 4 weeks)

| Proline concentration (%) | Number of days 0 | 3 | 7 | 14 | 28 | pH of solution on the 28th day | Osmotic pressure (Osm/kg) | Operability of solution |
|---|---|---|---|---|---|---|---|---|
| 0 | − | − | − | − | − | 6.5 | 0 | Good |
| 10 | − | + | + | + | + | 6.6 | 0.9 | Good |
| 20 | − | − | + | + | + | 6.6 | 1.8 | Good |
| 30 | − | − | + | + | + | 6.6 | 2.7 | Good |
| 40 | − | − | − | + | + | 6.6 | 3.6 | Good |
| 50 | − | − | − | − | − | 6.9 | 4.5 | Good |

−: no appearance of fungi
+: Appearance of fungi

As shown above, when the proline concentration in an aqueous solution was 10% or more, the proliferation of microorganisms was suppressed. In addition, the proliferation of the microorganisms was further suppressed as the proline concentration increased, and when the proline concentration was about 50%, the proliferation of the microorganisms was prevented almost completely.

It should be noted that values of the pH of the aqueous proline solutions after four weeks were almost uniform, indicating that the proliferation of the microorganisms was not suppressed by the change in pH.

In addition, every solution had good operability, and no precipitation of crystals.

Example 2

The Effects of the Presence of Salts in a Proline Solution, and the Consequent Salt Damage to Plants The effects of contaminating salts in a proline solution and its relationship to salt damage was investigated using model solutions. For the model solutions, a solution obtained by removing cell bodies from a proline fermentation solution (hereinafter, simply referred to as the "proline fermentation solution") and a solution obtained by removing the contaminating salts from the fermentation solution (hereinafter, referred to as the "desalted solution") were used. Table 4 shows the composition of the proline fermentation solutions, and Table 5 shows the composition of the desalted solutions.

Komatsuna (i.e., *Brassica campestris* var. *peruviridis*) was cultivated in a pot (having a diameter of 7.5 cm and a depth of 6.5 cm) with a commercially available culture soil. 2.5 ml of each model solution was added once onto the surface of leaves of komatsuna, to confirm the degree of a salt damage.

Table 6 shows results obtained 18 hours after the dispersion.

TABLE 4

(units in Table are weight %)

|  | A | B |
|---|---|---|
| Proline | 0.02 | 0.002 |
| $KH_2PO_4$ | 0.00056 | 0.000056 |
| $(NH_4)_2SO_4$ | 0.03428 | 0.003428 |
| $MgSO_4 \cdot 7H_2O$ | 0.00024 | 0.000024 |
| NaCl | 0.00172 | 0.000172 |
| Water | 99.94 | 99.99 |
| Total inorganic salt concentration | 0.0368 | 0.00368 |

TABLE 5

(units in Table are weight %)

|  | C | D | E |
|---|---|---|---|
| Proline | 0.020 | 0.002 | 0.000 |
| Water | 99.980 | 99.998 | 100.00 |

TABLE 6

|  | A | B | C | D | E |
|---|---|---|---|---|---|
| Growth | Not good | Not good | Good | Good | Normal |

"Not good" indicates the withering of leaves or stems, i.e. unvigorous growth, as compared to Control Plot E
"Good" indicates vigorous leaves or stems, i.e. good growth, as compared to Control Plot E As described above, the salt damage to a plant was suppressed by decreasing the concentration of contaminating salts at any proline concentration. Also, higher concentration proline solutions were able to be dispersed. In addition, it was confirmed that the dispersion of a high concentration proline solution improves the growth of a plant.

INDUSTRIAL APPLICABILITY

The liquid fertilizers and a plant vitalizers of the present invention have excellent operability, can prevent contamination by microorganisms, and in addition, likely do not cause salt damage to a plant when applied thereto.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method of preserving an aqueous L-proline solution while avoiding contamination by microorganisms, comprising:
    adjusting the concentration of L-proline in the aqueous L-proline solution to 20% (w/w) or more.

2. The method according to claim 1, wherein the aqueous L-proline solution is obtained by culturing a bacterium having an L-proline-producing ability in a medium, removing cell bodies from the medium resulting in an L-proline solution, and concentrating the L-proline in the solution.

3. The method according to claim 2, wherein the aqueous L-proline solution is obtained by desalting the L-proline solution after removing the cell bodies and before concentrating the L-proline in the solution.

4. The method according to claim 1, wherein the concentration of L-proline in the aqueous L-proline solution is adjusted to between 20% and 80% (w/w).

5. The method according to claim 1, wherein the concentration of L-proline in the aqueous L-proline solution is adjusted to 40 to 70% (w/w).

6. The method according to claim 3, wherein the L-proline solution is desalted so that the weight ratio of contaminating salt to proline in the solution is 1 or less.

7. The method according to claim 3, wherein the L-proline solution is desalted so that the weight ratio of contaminating salt to proline in the solution is 0.5 or less.

8. The method according to claim 3, wherein the L-proline solution is desalted so that the weight ratio of contaminating salt to proline in the solution is 0.3 or less.

* * * * *